(12) United States Patent
Chen et al.

(10) Patent No.: US 9,772,222 B2
(45) Date of Patent: Sep. 26, 2017

(54) RETAINER FOR PHOTOELECTRIC SENSOR AND PHOTOELECTRIC PULSE WAVE MEASURING APPARATUS INCLUDING THE SAME

(71) Applicant: SAMSUNG ELECTRONICS CO., LTD., Suwon-si (KR)

(72) Inventors: Wen Xi Chen, Aizuwakamatsu (JP);
Takeshi Nagahiro, Yokohama (JP);
Yosuke Aoyagi, Yokohama (JP);
Naoyuki Takada, Yokohama (JP);
Takahiro Tokumiya, Yokohama (JP)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 14/959,111

(22) Filed: Dec. 4, 2015

(65) Prior Publication Data

US 2016/0157741 A1 Jun. 9, 2016

(30) Foreign Application Priority Data

Dec. 8, 2014 (JP) .................................. 2014-248191
Jan. 26, 2015 (KR) ........................ 10-2015-0012311

(51) Int. Cl.
*A61B 5/024* (2006.01)
*G01J 1/02* (2006.01)
*A61B 5/00* (2006.01)

(52) U.S. Cl.
CPC ........ *G01J 1/0271* (2013.01); *A61B 5/02427* (2013.01); *A61B 5/6843* (2013.01)

(58) Field of Classification Search
None
See application file for complete search history.

(56) References Cited

U.S. PATENT DOCUMENTS

| 5,119,822 | A  | * | 6/1992 | Niwa | A61B 5/021 600/485 |
| 6,932,772 | B2 | * | 8/2005 | Kan | A61B 5/02116 600/485 |
| 7,103,407 | B2 |   | 9/2006 | Hjelt et al. | |
| 7,425,199 | B2 |   | 9/2008 | Hoctor et al. | |
| 7,674,230 | B2 |   | 3/2010 | Reisfeld | |

(Continued)

FOREIGN PATENT DOCUMENTS

| JP | 2656781 B2 | 9/1997 |
| JP | 09-299339 A | 11/1997 |

(Continued)

*Primary Examiner* — Brian T Gedeon
(74) *Attorney, Agent, or Firm* — Sughrue Mion, PLLC

(57) ABSTRACT

A photoelectric sensor retainer and a photoelectric pulse wave measuring apparatus including the same are provided. The photoelectric sensor retainer includes a sensor mounting unit on which a photoelectric sensor having a light-receiving surface is attachable and detachable, the light-receiving surface facing a measuring direction. The photoelectric sensor retainer further includes a pressing unit configured to press an upper surface of the sensor mounting unit in the measuring direction to apply pressure to the sensor mounting unit, and a pedestal including a seating plate configured to support the pressing unit, the seating plate having a principal plane perpendicular to a pressing direction of the pressing unit.

12 Claims, 10 Drawing Sheets

(56) References Cited

U.S. PATENT DOCUMENTS

| | | | |
|---|---|---|---|
| 8,355,767 B2 | 1/2013 | Hunter et al. | |
| 8,591,424 B2* | 11/2013 | Bae | A61B 5/02141 600/485 |
| 9,107,593 B2 | 8/2015 | Tamada | |
| 9,445,732 B2* | 9/2016 | Lee | A61B 5/0255 |
| 9,476,961 B2 | 10/2016 | Kang et al. | |
| 2004/0010199 A1* | 1/2004 | Hashimoto | A61B 5/02 600/502 |
| 2008/0103398 A1* | 5/2008 | Huang | A61B 5/02444 600/500 |
| 2010/0179439 A1 | 7/2010 | Kuschel et al. | |
| 2011/0282219 A1 | 11/2011 | Parzy et al. | |
| 2011/0306889 A1* | 12/2011 | Di | A61B 5/6835 600/499 |
| 2012/0184860 A1* | 7/2012 | Pan | A61B 5/02 600/500 |
| 2016/0015282 A1 | 1/2016 | Kim et al. | |
| 2016/0054423 A1 | 2/2016 | Kang et al. | |
| 2016/0310021 A1* | 10/2016 | Kato | A61B 5/02108 |

FOREIGN PATENT DOCUMENTS

| | | |
|---|---|---|
| JP | 2002-224064 A | 8/2002 |
| JP | 2005-040259 A | 2/2005 |
| JP | 2008-061830 A | 3/2008 |
| JP | 4325638 B2 | 9/2009 |
| JP | 2010-131247 A | 6/2010 |
| JP | 2011-050745 A | 3/2011 |
| JP | 2013-132437 A | 7/2013 |
| JP | 2013-150772 A | 8/2013 |
| JP | 5570013 B2 | 8/2014 |

* cited by examiner

RETAINER FOR PHOTOELECTRIC SENSOR AND PHOTOELECTRIC PULSE WAVE MEASURING APPARATUS INCLUDING THE SAME

CROSS-REFERENCE TO RELATED APPLICATIONS

This application claims priority from Japanese Patent Application No. 2014-248191, filed on Dec. 8, 2014, in the Japanese Patent Office, and Korean Patent Application No. 10-2015-0012311, filed on Jan. 26, 2015, in the Korean Intellectual Property Office, the disclosures of which are incorporated herein by reference in their entireties.

BACKGROUND

1. Field

Apparatuses consistent with exemplary embodiments relate to a retainer for supporting a photoelectric sensor and a photoelectric pulse wave measuring apparatus including the retainer.

2. Description of the Related Art

Japanese Patent Application Publication No. 2005-040259 discloses a pulse wave measuring apparatus as an example of a photoelectric pulse wave measuring apparatus. The pulse wave measuring apparatus includes a light emitter and a photoelectric sensor. The light emitter includes a light-emitting device that emits, for example, near infrared rays to a blood vessel. The near infrared rays are reflected by the blood vessel. The photoelectric sensor includes a light receiver that receives the reflected light.

The pulse wave measuring apparatus, as described in lines 12 to 27 on page 6 of the Japanese Patent Application Publication, is only used for measuring the number of pulses. Also, because it is lightweight, the number of pulses may be measured during exercise.

The related art has been further developed to a degree that a biomarker can be estimated from a waveform of a pulse wave and the waveform of the pulse wave may be accurately measured. Hereinafter, a description of the development will be described.

FIG. 1 is a schematic drawing of a photoelectric sensor retainer 14 of the related art. The photoelectric sensor retainer 14 includes a pedestal 19 of a photoelectric sensor 75 and a band 90 which is combined with the pedestal 19. The photoelectric sensor 75 is mounted on the pedestal 19. The band 90 may be formed of a resin.

The photoelectric sensor retainer 14 is mounted around a forearm 95. FIG. 1 shows a wrist of the forearm 95. When the band 90 is tightened, the photoelectric sensor 75 contacts a skin surface 96 of the forearm 95.

To precisely measure a pulse wave by using the photoelectric sensor 75 of FIG. 1, a state is provided in which paths of irradiating light and diffusing light do not deviate from each other. This state is maintained for a period of measuring the pulse wave. Accordingly, when the pulse wave is measured, a light emitter 80 and the photoelectric sensor 75 tightly contact the skin surface 96. Also, a pressing force is such a degree that an optic axis of the irradiating light does not deviate.

Therefore, it is desired that a light-receiving surface 77 of the photoelectric sensor 75 is in contact with the skin surface 96 near a radial artery 97 of the forearm 95. The light-receiving surface 77 may face a predetermined measuring direction 74. The predetermined measuring direction 74 may be a parallel direction to a perpendicular line of the skin surface 96.

However, the shape of the skin surface 96 may vary according to age, sex, and physical constitution of a person under examination. Therefore, it is difficult to press the photoelectric sensor 75 near the radial artery 97 in the predetermined measuring direction 74 by simply tightening the band 90.

This is because the tightening of the band 90 cannot control the magnitude and the direction of force that is applied to the photoelectric sensor 75. That is, because the position of the photoelectric sensor 75 on the band 90 is variable, the force provided by the band 90 is dispersed due to the principle of action and reaction.

It can be considered that the above problem may be solved by adding an electrical pressing device after increasing the size of the photoelectric sensor retainer 14 of FIG. 1. However, it is difficult to make the photoelectric sensor retainer 14 lightweight enough to be applied to a portable device.

SUMMARY

Exemplary embodiments address at least the above problems and/or disadvantages and other disadvantages not described above. Also, the exemplary embodiments are not required to overcome the disadvantages described above, and may not overcome any of the problems described above.

Aspects of the exemplary embodiments provide a retainer for a photoelectric sensor and a photoelectric pulse wave measuring apparatus including the same.

Additional aspects will be set forth in part in the description which follows and, in part, will be apparent from the description, or may be learned by practice thereof.

According to an aspect of an exemplary embodiment, there is provided a photoelectric sensor retainer including a sensor mounting unit on which a photoelectric sensor having a light-receiving surface is attachable and detachable, the light-receiving surface facing a measuring direction. The photoelectric sensor retainer further includes a pressing unit configured to press an upper surface of the sensor mounting unit in the measuring direction to apply pressure to the sensor mounting unit, and a pedestal including a seating plate configured to support the pressing unit, the seating plate having a principal plane perpendicular to a pressing direction of the pressing unit.

The pressing unit may be screw combined with the seating plate, and an edge of the pressing unit may be configured to press the upper surface of the sensor mounting unit while the pressing unit is rotated to adjust a distance between the seating plate and the upper surface of the sensor mounting unit.

The photoelectric sensor retainer may further include a suspension device configured to support the sensor mounting unit. The suspension device may include a frame disposed to face the sensor mounting unit with the seating plate therebetween, and links configured to connect the frame and the sensor mounting unit, and pass through the seating plate.

The photoelectric sensor retainer may further include coil springs surrounding the links between the seating plate and the frame, and the coil springs may repulse the sensor mounting unit in a direction opposite to the measuring direction.

The links may include four or more links, and the links may surround the pressing unit.

The photoelectric sensor retainer may further include a band connected to the pedestal. The pedestal may include adjusting units, each of the adjusting units being configured to adjust an angle between the principal plane and a plane of the band, and wings disposed on respective edges of the seating plate. Ends of the band may be connected to the respective wings, the measuring direction may be oriented inside a ring that is formed by the band and the pedestal, and the pedestal may be configured to rotate around each of the wings with respect to the band.

The adjusting units may be disposed on the respective wings, and each of the adjusting units may be configured to adjust a distance between a rotational axis of a respective one of the wings and the principal plane.

The photoelectric sensor retainer may further include pins, each of the pins forming the rotational axis. Each of the adjusting units may include holes having respective distances from the principal plane, and each of the pins may be configured to be attached to and detached from a respective one of the holes.

The sensor mounting unit may include a base unit, a sensor supporting unit disposed on a side of the base unit in the measuring direction, the sensor supporting unit including a sensor supporting surface disposed to face the measuring direction, and a piezoelectric element disposed between the base unit and the sensor supporting unit.

The photoelectric sensor retainer may further include a stage configured to support the pedestal, a forearm supporter disposed on a side of the sensor mounting unit in the measuring direction, the forearm supporter being configured to support a forearm so that a radial artery of the forearm faces the sensor mounting unit, and supporting columns configured to support the stage, the supporting columns being connected to the forearm supporter. The stage may be configured to move in the measuring direction and in a direction opposite to the measuring direction with respect to the supporting columns.

The stage may be configured to rotate around a rotational axis perpendicular to a plane parallel with a length direction of the forearm supporter and the measuring direction.

The stage may include protrusion portions extending in a direction of the rotational axis toward the supporting columns, the supporting columns may include respective grooves corresponding to the respective protrusion portions, and the protrusion portions may be connected to the respective supporting columns by respective fixing elements configured to fix locations of the respective protrusion portions on the respective supporting columns and rotating locations of the respective protrusion portions with respect to the rotational axis.

A photoelectric pulse wave measuring apparatus may include the photoelectric sensor retainer, and a photoelectric sensor having the light-receiving surface and a substrate surface on a side opposite to the light-receiving surface, the photoelectric sensor disposed on the sensor supporting surface. The substrate surface may be disposed to face the sensor supporting surface.

BRIEF DESCRIPTION OF THE DRAWINGS

The above and other aspects will become apparent and more readily appreciated from the following description of the exemplary embodiments, taken in conjunction with the accompanying drawings of which.

DETAILED DESCRIPTION OF THE EXEMPLARY EMBODIMENTS

Figure 1:
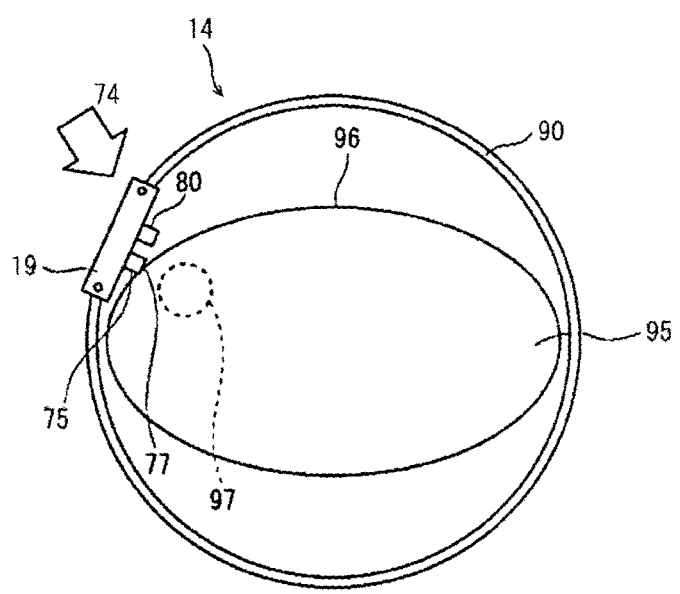
FIG. 1 is a schematic drawing of a photoelectric sensor retainer of the related art.

Reference will now be made in detail to the exemplary embodiments, examples of which are illustrated in the accompanying drawings. In the drawings, like reference numerals refer to like elements throughout. Also, like reference numerals are used to indicate elements that are of the same quality but of different locations and dispositions, and these are differentiated by adding alphabet letters at ends of the reference numerals. Accordingly, descriptions of the same constituent elements and the same quality of constituent elements will not be repeated.

The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail because they would obscure the description with unnecessary detail.

Figure 2:
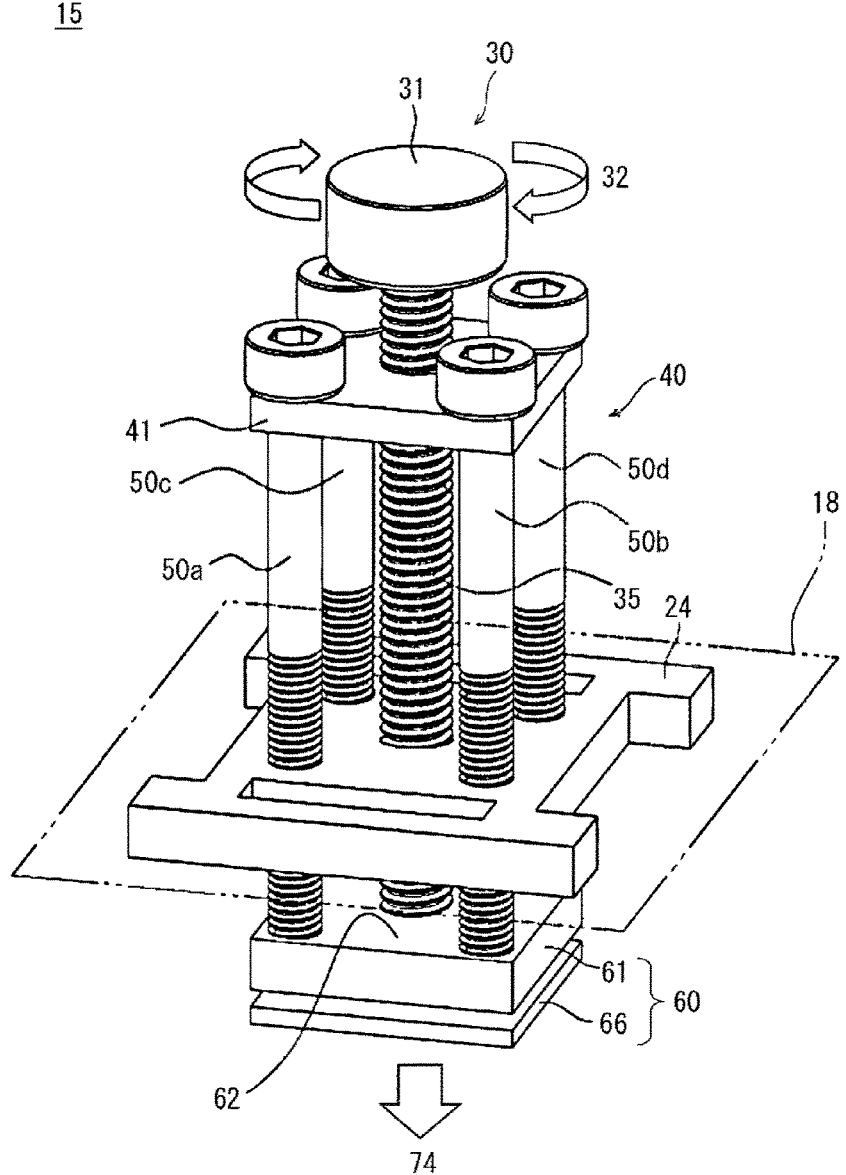
FIG. 2 is a perspective view of a photoelectric sensor retainer according to an exemplary embodiment.

FIG. 2 is a perspective view of a photoelectric sensor retainer 15 according to an exemplary embodiment. The photoelectric sensor retainer 15 includes a mounting unit 60, a pressing unit 30, and a seating plate 24. The mounting unit 60 may be used for a photoelectric sensor. The photoelectric sensor is attached to and detached from the mounting unit 60. The photoelectric sensor may be a light receiver having a light-receiving surface. The photoelectric sensor retainer 15 may be used as a photoelectric pulse wave measuring apparatus by installing a photoelectric sensor and a light emitter on the photoelectric sensor retainer 15.

The mounting unit 60 is located on a lower side of the seating plate 24. The mounting unit 60 includes a base unit 61 and a supporting unit 66. The supporting unit 66 is located on a side of a measuring direction 74 with respect to the base unit 61. The base unit 61 has an upper surface 62.

The pressing unit 30 of FIG. 2 includes a head unit 31 and an axis unit 35. The head unit 31 and the axis unit 35 may be a bolt formed as one body. Thread grooves may be formed on the axis unit 35. A direction of the thread grooves may be in a right-handed screw direction. The axis unit 35 is screw coupled to a hole formed in the seating plate 24.

A direction 32 shown in FIG. 2 is a clockwise direction with respect to a center axis of the axis unit 35 when viewed from a plan view. When the head unit 31 is rotated in the direction 32, the axis unit 35 is rotated in the direction 32, and the pressing unit 30 is forwarded in the same direction as the measuring direction 74 with respect to the seating plate 24.

As shown in FIG. 2, when the head unit 31 is rotated in the direction 32, the pressing unit 30 presses the upper surface 62. The seating plate 24 supports the pressing unit 30. The pressing unit 30 contacts the seating plate 24 at a location where the pressing unit 30 passes through the seating plate 24.

A photoelectric sensor may be mounted on the mounting unit 60 of FIG. 2 so that a light-receiving surface of the photoelectric sensor faces the measuring direction 74. A surface of a skin of the forearm may be located in front of the measuring direction 74. The measuring direction 74 may be parallel to a perpendicular line of the surface of the skin.

The mounting unit 60 is pressed in the same direction of the measuring direction 74 by the pressing unit 30 of FIG. 2. The seating plate 24 has a principal plane 18. The principal plane 18 is parallel to a plane perpendicular to a pressing direction by the pressing unit to the mounting unit 60. The mounting unit 60 may have an area greater than that of the pressing unit 30 when viewed from a plan view.

The base unit 61 of FIG. 2 is combined with a suspension device 40. The suspension device 40 supports the mounting unit 60. The suspension device 40 may include an element that makes the mounting unit 60 repulse in an opposite direction to the measuring direction 74. That is, the suspension device 40 provides a repulsion force against the mounting unit 60 in an opposite direction to the pressing force by the pressing unit 30. The element may be buffers 70a and 70b depicted in FIG. 4.

Because the mounting unit 60 has an area greater than that of the pressing unit 30, it is difficult for the pressing unit 30 to press the mounting unit 60 in a state that a light-receiving surface is maintained in an appropriate direction. Here, the maintaining of the appropriate direction of the light-receiving surface denotes maintaining the light-receiving surface of the photoelectric sensor as an perpendicular plane to the measuring direction 74 or maintaining the light-receiving surface of the photoelectric sensor parallel to a surface of a skin.

When the light-receiving surface 77 is not maintained in the appropriate direction as depicted in FIG. 1, the mounting unit 60 may be pressed in an inclined position due to stress that works with respect to the photoelectric sensor 75 from the skin surface 96. In this case, a tight contact between the light-receiving surface 77 and the skin surface 96 is not acquired.

In the case of FIG. 1, reflection light from a blood vessel may not be reach to the light-receiving surface 77 because the reflection light leaks through a gap between the light-receiving surface 77 and the skin surface 96. Therefore, a ratio of signal/noise may be reduced. Also, external disturbance light may penetrate into the gap between the light-receiving surface 77 and the skin surface 96. When there is a photoelectric conversion of the external disturbance light, noise with respect to pulse wave signal will be newly generated.

When taking into consideration of this problem, the suspension device 40 of FIG. 2 may support the mounting unit 60 on 3 points or more. The suspension device 40 may surround the pressing unit 30 when viewed from a plan view.

The suspension device 40 of FIG. 2 includes a frame 41 and links 50a, 50b, 50c, and 50d. The frame 41 is disposed above the seating plate 24. The links 50a, 50b, 50c, and 50d are disposed below the frame 41.

The links 50a, 50b, 50c, and 50d of FIG. 2 are located between the frame 41 and the mounting unit 60. The links 50a, 50b, 50c, and 50d respectively are combined with the frame 41 and the mounting unit 60. The links 50a, 50b, 50c, and 50d surround the pressing unit 30. The links 50a, 50b, 50c, and 50d may be configured as bolts.

In the photoelectric sensor retainer 15 of FIG. 2, the pressing unit 30 presses the mounting unit 60. Therefore, when compared to the case when there is no pressing unit 30, it is possible for the light-receiving surface of the photoelectric sensor that is mounted on the mounting unit 60 to be further tightly in contact with the skin surface of a forearm.

Also, in the photoelectric sensor retainer 15 of FIG. 2, the suspension device 40 corrects a difference between the pressing direction of the pressing unit 30 and the measuring direction 74. Therefore, when compared to a case that there is no suspension device 40, the photoelectric sensor may be pressed along a direction close to parallel to the skin surface of the forearm.

Also, in the photoelectric sensor retainer 15 of FIG. 2, while the light-receiving surface is maintained in the appropriate direction, the pressing unit 30 may press the mounting unit 60. The description of the suspension device 40 will be made in another exemplary embodiment in which the same suspension device 40 is used.

Referring to FIGS. 3 through 7, another exemplary embodiment will be described.

Figure 3:
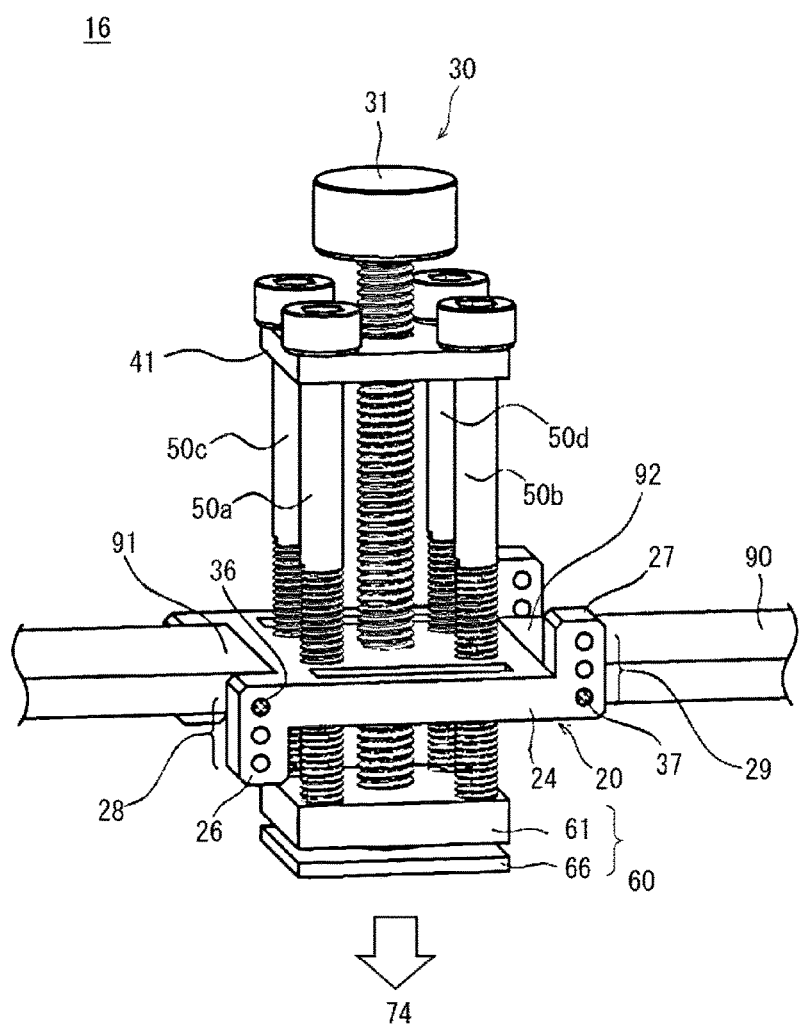
FIG. 3 is a perspective view of a photoelectric sensor retainer according to another exemplary embodiment.

FIG. 3 is a perspective view of a photoelectric sensor retainer 16 according to the other exemplary embodiment. The photoelectric sensor retainer 16 further includes a band 90 and wings 26 and 27 when compared to the photoelectric sensor retainer 15 of FIG. 2.

The photoelectric sensor retainer 16 of FIG. 3 includes a pedestal 20. The pedestal 20 includes the wing 26 formed on an edge of the seating plate 24 and the wing 27 formed on the other edge of the seating plate 24. The band 90 is connected to the pedestal 20 on the wings 26 and 27. Each of the wings 26 and 27 includes a pair of wings facing each other with a predetermined gap.

The band 90 of FIG. 3 includes a first edge 91 and a second edge 92. The first edge 91 is connected to the wing 26. The second edge 92 is connected to the wing 27. The first edge 91 and the second edge 92 may be disposed between the corresponding pair of wings of the wings 26 and 27.

The photoelectric sensor retainer 16 of FIG. 3 includes a pin 36. The pin 36 constitutes a rotational axis. The pedestal 20 is rotatable with respect to the band 90 with the pin 36 as the center.

The photoelectric sensor retainer 16 of FIG. 3 includes a pin 37. The pin 37 constitutes a rotational axis. The pedestal 20 is rotatable around the pin 37 with respect to the band 90.

The photoelectric sensor retainer 16 of FIG. 3 includes adjusting units 28 and 29. The adjusting units 28 and 29 are respectively located on the wings 26 and 27. The pins 36 and 37 are respectively attachable to and detachable from holes that are formed in the adjusting units 28 and 29. The pins 36 and 37 are readily attachable and detachable and allow the adjusting units 28 and 29 to readily control an inclination of the seating plate 24.

Figure 4:
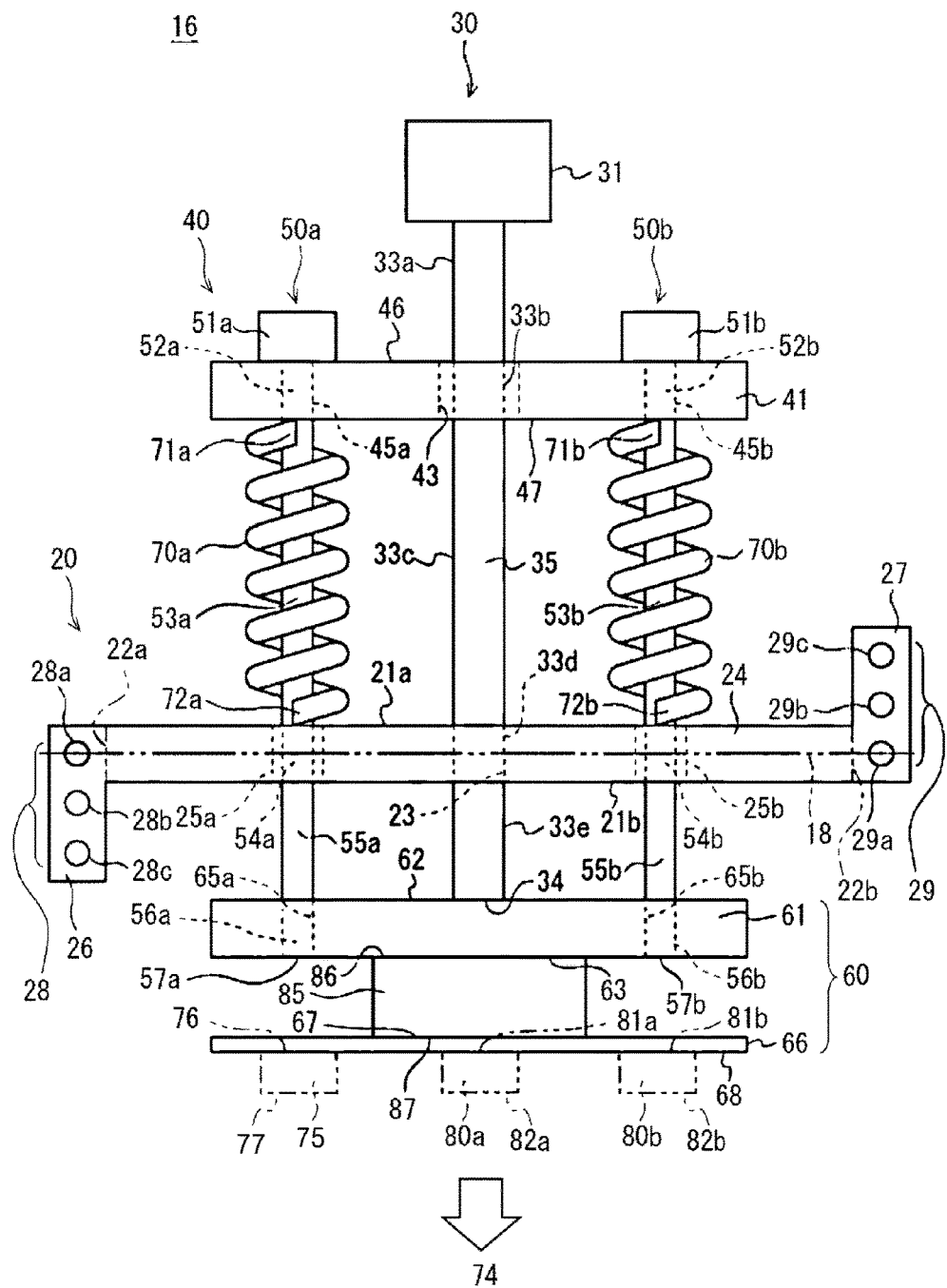
FIG. 4 is a cross-sectional view of the photoelectric sensor retainer of FIG. 3.

FIG. 4 is a cross-sectional view of the photoelectric sensor retainer 16 of FIG. 3. Some elements of the photoelectric sensor retainer 16 are omitted in FIG. 4.

The suspension device 40 of FIG. 4 includes the links 50a and 50b, and buffers 70a and 70b. In FIG. 4, the links 50c and 50d shown in FIGS. 2 and 3 are covered by the links 50a and 50b.

Also, the links 50c and 50d shown in FIGS. 2 and 3 include buffers as the same as the buffers 70a and 70b of FIG. 4. In the descriptions below, the links 50a and 50b and members and locations related to the links 50a and 50b will be described. However, the links 50c and 50d and members and locations related to the links 50c and 50d also have the same configuration as related to the links 50a and 50b.

The seating plate 24 included in the pedestal 20 of FIG. 4 includes an upper surface 21a and a lower surface 21b. The seating plate 24 includes a plurality of holes. The holes pass through the seating plate 24. A hole surface 23 and hole surfaces 25a and 25b respectively are formed in the holes. Thread grooves respectively may be formed on each of the hole surface 23 and hole surfaces 25a and 25b. The direction of the thread grooves may be in a right-handed screw direction.

The wing 26 of the pedestal 20 of FIG. 4 contacts an edge 22a of the seating plate 24. The wing 27 of the pedestal 20 contacts another edge 22b of the seating plate 24.

The frame 41 of FIG. 4 includes an upper surface 46 on an opposite side to the measuring direction 74 and a lower surface 47 facing the measuring direction 74. The frame 41 includes a plurality of holes. The holes pass through the frame 41. A hole surface 43 and hole surfaces 45a and 45b respectively are formed in the holes. Thread grooves respectively may be formed on each of the hole surface 43 and hole surfaces 45a and 45b. The direction of the thread grooves may be in a right-handed screw direction.

The base unit 61 of FIG. 4 includes a lower surface 63. The base unit 61 includes a plurality of holes. The holes pass through the base unit 61. The holes may not pass through the base unit 61. Hole surfaces 65a and 65b are respectively formed in the holes. Thread grooves may be formed on the hole surfaces 65a and 65b.

The supporting unit 66 of FIG. 4 includes a supporting surface 68 which is a lower surface thereof. The supporting surface 68 is a sensor supporting surface that faces the measuring direction 74. The supporting unit 66 includes an upper surface 67 on an opposite side to the supporting surface 68.

The axis unit 35 of the pressing unit 30 of FIG. 4 includes axis surfaces 33a, 33b, 33c, 33d, and 33e and a cross-sectional surface 34 in the stated order from the head unit 31. The axis surfaces 33a, 33b, 33c, 33d, and 33e are the same axis surfaces. The alphabets are used only for convenience of differentiating the location relationship between the axis surfaces 33a, 33b, 33c, 33d, and 33e and the frame 41, the seating plate 24, and the base unit 61.

The axis surface 33a of FIG. 4 is located above the upper surface 46 of the frame 41. The axis unit 35 includes a portion on which the axis surface 33a is formed to separate the head unit 31 from the frame 41. The head unit 31 is formed to be readily held by the user of the photoelectric sensor retainer 16.

The axis surface 33b of FIG. 4 is located inside of the hole surface 43 of the frame 41. The axis surface 33b is not in contact with the hole surface 43. Even though the axis surface 33b and the hole surface 43 contact each other, a friction interrupting the change of location of the pressing unit 30 with respect to the frame 41 may not occur.

The axis surface 33c of FIG. 4 is located below the lower surface 47 of the frame 41 and is located above the upper surface 21a of the seating plate 24. The axis surface 33c may be surrounded by another buffer (not shown) as the buffers 70a and 70b.

The axis surface 33d of FIG. 4 is located inside of a hole surface 23 of the seating plate 24. Thread grooves may be formed at least on the axis surface 33d and the axis surfaces 33c and 33e in a region close to the axis surface 33d.

As described above, the axis surface 33d and the hole surface 23 of FIG. 4 are screw combined. There is a friction force between the axis surface 33d and the hole surface 23. The friction force does not interrupt the rotation of the head unit 31 when the user operates the photoelectric sensor retainer 16. The friction force maintains the location of the pressing unit 30 after operating the pressing unit 30 in the measuring direction 74 or in an opposite direction to the measuring direction 74.

The axis surface 33e of FIG. 4 is located below the lower surface 21b of the seating plate 24 and is located above the upper surface 62 of the base unit 61. The axis surface 33e is adjacent to the cross-sectional surface 34. A length of a portion (i.e., an edge) of the axis unit 35 on which the axis surface 33e is formed is changed according to the rotation of the axis unit 35. The portion of the axis unit 35 adjusts a distance between the lower surface 21b and the upper surface 62.

The cross-sectional surface 34 of FIG. 4 contacts the upper surface 62 of the base unit 61. The pressing unit 30 presses the upper surface 62 on the cross-sectional surface 34. The cross-sectional surface 34 may contact on a center of the mounting unit 60. Accordingly, it is easy for the pressing unit 30 to press the mounting unit 60 in the same direction as the measuring direction 74.

The links 50a and 50b of FIG. 4 respectively includes head unit 51a and 51b and an axis unit. The axis unit of the links 50a and 50b includes axis surfaces 52a and 52b, axis surfaces 53a and 53b, axis surfaces 54a and 54b, axis surfaces 55a and 55b, axis surfaces 56a and 56b, and axis surfaces 57a and 57b in the stated order from each of the head units 51a and 51b.

The links 50a and 50b may be bolts in which the head units 51a and 51b and the axis unit are respectively formed as one body. The axis units may have thread grooves. The direction of the thread grooves may be in a right-handed screw direction. The thread grooves may be formed at least on the axis surfaces 52a and 52b and the axis surfaces 56a and 56b.

The axis surfaces 52a and 52b, the axis surfaces 53a and 53b, the axis surfaces 54a and 54b, the axis surfaces 55a and 55b, and the axis surfaces 56a and 56b respectively are the same axis surfaces with respect to the links 50a and 50b of FIG. 4. The numeral numbers of the axis surfaces 53a and 53b, the axis surfaces 54a and 54b, and the axis surfaces 55a and 55b are used only for convenience of differentiating the location relationship between the axis surfaces and the frame 41, the seating plate 24, and the base unit 61.

The head units 51a and 51b of FIG. 4 respectively contact the upper surface 46 of the frame 41. The head units 51a and 51b are used for rotating the links 50a and 50b when the links 50a and 50b are screw combined with the frame 41 and the base unit 61. The head units 51a and 51b may be omitted.

The axis surfaces 52a and 52b of FIG. 4 are respectively screw combined with the hole surfaces 45a and 45b. There is a friction force between the axis surfaces 52a and 52b and the hole surfaces 45a and 45b. The friction force fixes the links 50a and 50b on the frame 41.

Instead of respectively combining the axis surfaces 52a and 52b and the hole surfaces 45a and 45b of FIG. 4, the links 50a and 50b may be welded to the frame 41. In this case, the axis surfaces 52a and 52b and the hole surfaces 45a and 45b respectively may not necessarily include thread grooves.

The axis surfaces 53a and 53b of FIG. 4 are respectively located below the lower surface 47 of the frame 41 and above the upper surface 21a of the seating plate 24.

The axis surfaces 54a and 54b respectively may be located inside the hole surfaces 25a and 25b of the seating plate 24. The axis surfaces 54a and 54b may not be in contact with the hole surfaces 25a and 25b. Also, although the axis surfaces 54a and 54b respectively are in contact with the hole surfaces 25a and 25b, a friction force interrupting the location change of the frame 41 and the mounting unit 60 with respect to the seating plate 24 may not occur.

The axis surfaces 55a and 55b of FIG. 4 respectively are located below the lower surface 21b of the seating plate 24 and above the upper surface 62 of the base unit 61. The axis surfaces 55a and 55b respectively are adjacent to the cross-sectional surfaces 57a and 57b.

The axis surfaces 56a and 56b of FIG. 4 respectively are screw combined with hole surfaces 65a and 65b. There is a friction force between the axis surfaces 56a and 56b and the hole surfaces 65a and 65b. The friction force fixes the links 50a and 50b on the base unit 61.

Instead of respectively screw combining the axis surfaces 56a and 56b and the hole surfaces 65a and 65b of FIG. 4, the links 50a and 50b may be welded to the base unit 61. In this case, the axis surfaces 56a and 56b and the hole surfaces 65a and 65b respectively may not necessarily include thread grooves.

The cross-sectional surfaces 57a and 57b of FIG. 4 respectively are exposed on the lower surface 63 of the base unit 61. If holes that are related to the hole surfaces 65a and 65b are not passing through the base unit 61, the cross-sectional surfaces 57a and 57b may be located inside the base unit 61. Also, the axis surfaces 56a and 56b and the hole surfaces 65a and 65b may be omitted. In this case, the cross-sectional surfaces 57a and 57b respectively may be joined on the upper surface 62 of the base unit 61.

The buffers 70a and 70b of FIG. 4 respectively may be coil springs that form a spiral with the axis surfaces 53a and 53b as centers. The spring coils may be in a compressed state when the spring coils are installed on the suspension device.

The buffers 70a and 70b of FIG. 4 respectively include upper edges 71a and 71b and lower edges 72a and 72b. The upper edges 71a and 71b respectively contact the lower surface 47 of the frame 41. The upper edges 71a and 71b respectively may be or may not be fixed on the lower surface 47. The lower edges 72a and 72b respectively contact the upper surface 62 of the base unit 61. The lower edges 72a and 72b may be or may not be fixed on the upper surface 62.

The adjusting unit 28 of FIG. 4 includes a plurality of holes 28a, 28b, and 28c respectively having different distances from the principal plane 18. The distances between the holes 28a, 28b, and 28c and the principal plane 18 are gradually increased in the order of the holes 28a, 28b, and 28c. The adjusting unit 29 includes a plurality of holes 29a, 29b, and 29c respectively having different distances from the principal plane 18. The distances between the holes 29a, 29b, and 29c and the principal plane 18 are gradually increased in the order of the holes 29a, 29b, and 29c. The holes 28a, 28b, and 28c and the holes 29a, 29b, and 29c respectively may penetrate or may not penetrate through the wings 26 and 27.

That pedestal 20 that is configured of the seating plate 24 and the wings 26 and 27 has a crank shape. That is, when the photoelectric sensor retainer 16 is viewed from the front, a length direction of the wings 26 and 27 may be perpendicular to a plane that is parallel to the principal plane 18 of the seating plate 24. Also, the wing 26 may extend in a downward direction from the principal plane 18, and the wing 27 may extend in an upward direction from the principal plane 18.

Also, at least one of the wings 26 and 27 of FIG. 4 may extend in an upward and downward direction from the principal plane 18. That is, the pedestal 20 configured of the seating plate 24 and the wings 26 and 27 may have an H shape.

The holes 28a, 28b, and 28c and the holes 29a, 29b, and 29c respectively may be formed along the length direction of the wings 26 and 27. That is, the holes 28a, 28b, and 28c and the holes 29a, 29b, and 29c respectively may be arranged in a direction perpendicular to a plane that is parallel to the principal plane 18.

Also, as shown in FIG. 3, the wings 26 and 27 respectively include a pair of wings. Therefore, holes may be formed in both wings thereof. That is, as shown in FIG. 3, holes are formed in front and rear sides of the wings 26 and 27.

The mounting unit 60 of FIG. 4 includes one or more piezoelectric elements 85. The piezoelectric element 85 is located between the base unit 61 and the supporting unit 66. The piezoelectric element 85 includes an upper surface 86 that is in contact with the lower surface 63 of the base unit 61. The piezoelectric element 85 includes a lower surface 87 that is in contact with the upper surface 67 of the supporting unit 66.

As depicted in FIG. 4, a photoelectric pulse wave measuring apparatus may be configured by installing the photoelectric sensor 75 and light emitters 80a and 80b on the supporting surface 68 of the supporting unit 66. The photoelectric pulse wave measuring apparatus may measure a volume of a predetermined region in a blood vessel.

The number of mounting photoelectric sensors may be one, two, three, or more. The number of mounting light emitters may be one, two, three, or more. The arrangement of the photoelectric sensors and the light emitters is not specifically limited. The photoelectric sensors and the light emitters may be arranged in one module. The attachment and detachment of the photoelectric sensors and the light emitters to and from the supporting surface 68 of the supporting unit 66 may be readily performed by using the module.

When the light emitters 80a and 80b of FIG. 4 emit a green light, a gap between the photoelectric sensor 75 and the light emitters 80a and 80b may be, for example, greater than 2 mm and below 3 mm. When the light emitters 80a and 80b emit a red light, the gap may be near 5 mm, or greater than 4.5 mm and below 5.5 mm.

As depicted in FIG. 4, the photoelectric pulse wave measuring apparatus may include the photoelectric sensor retainer 16, the one photoelectric sensor 75, and the two light emitters 80a and 80b. The light emitters 80a and 80b may emit light having different wave peaks. The photoelectric sensor 75 may perform a photoelectric conversion by receiving light having different wave peaks.

The photoelectric sensor 75 includes the light-receiving surface 77. The photoelectric sensor 75 includes a substrate surface 76 on an opposite side to the light-receiving surface 77. The photoelectric sensor 75 is mounted on the mounting unit 60. The substrate surface 76 faces the supporting surface 68.

The light emitters 80a and 80b of FIG. 4 include light-emitting surfaces 82a and 82b, respectively. The light emitters 80a and 80b include substrate surfaces 81a and 81b, respectively, on an opposite side to the light-emitting surfaces 82a and 82b. The light emitters 80a and 80b are mounted on the mounting unit 60. The substrate surfaces 81a and 81b face the supporting surface 68.

The light emitters 80a and 80b of FIG. 4 may be light-emitting diodes (LEDs) that are suitable for reducing weight of the photoelectric pulse wave measuring apparatus. The light emitters 80a and 80b may irradiate light, for example, light having a single wavelength or a single wave peak.

The light emitters 80a and 80b of FIG. 4 irradiates light into a living body, i.e., into a skin of a forearm or a blood vessel. The light is reflected in the living body, i.e., in a skin of a forearm or a blood vessel. The light diffuses when it is reflected. The photoelectric sensor 75 converts the diffused light into an electrical signal by receiving the diffused light. The photoelectric pulse wave measuring apparatus may calculate a pulse wave from the electrical signal by using a predetermined method.

The pressing unit 30 of FIG. 4 presses the upper surface 62 at a predetermined force. Therefore, the photoelectric sensor 75 and the light emitters 80a and 80b that are mounted on the mounting unit 60 are pressed by the predetermined force in the measuring direction 74. The predetermined force may be adjusted to be applied to a degree of pressure similar to a blood pressure of a measuring area. When an area of the upper surface 62 is approximately 0.5 $cm^2$, the predetermined force may be in a range from about 0.5 N to about 1.5 N, preferably in a range from about 0.9 N to about 1.1 N, and more preferably, may be 1.0 N.

Because a surface texture of a skin is not always the same, an area onto which pressure is applied may be as small as not to disturb a location relationship between the light-receiving surface 77 and the light-emitting surfaces 82a and 82b. Accordingly, to satisfy items related to the predetermined force of the pressing unit 30 described above, the predetermined force may be empirically obtained after optimizing a surface shape of the pressing unit 30 and the area of the upper surface 62.

The piezoelectric element 85 of FIG. 4 may bring reproducibility of pressure that is applied to a blood vessel when a pulse wave is measured. That is, when the pulse waves are measured for several times by adjusting the location of the pressing unit 30, pressures that are respectively applied to blood vessels may be adjusted to be uniform. Therefore, the degree of accuracy of the pulse wave measurement is increased, and a bias of collected data may be reduced.

Figure 5:
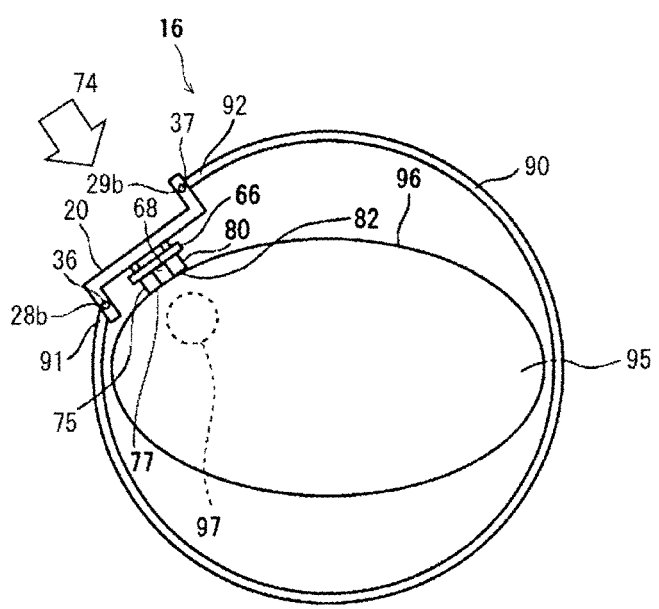
FIG. 5 is a front view illustrating a use of the photoelectric sensor retainer of FIG. 3.

FIG. 5 is a front view illustrating a use of the photoelectric sensor retainer 16 of FIG. 3. Some members included in the photoelectric sensor retainer 16 are omitted in FIG. 5. The band 90 and the pedestal 20 may form a ring. The measuring direction 74 faces inside of the ring that is formed by the band 90 and the pedestal 20. A light-emitting surface 82 of the light emitter 80, and a light-receiving surface 77 is located inside the ring.

The band 90 of FIG. 5 may be a belt or a band formed of a resin. The band 90 has a predetermined elasticity or strength, and thus, may maintain a location relationship between the pedestal 20 and the forearm. Because it is difficult to resist against stress when pressing by the pressing unit 30 of FIG. 3, the band 90 may not have elasticity of rubber.

A length of the band 90 of FIG. 5 may be adjusted. Accordingly, pulse waves of a plurality of persons under examination having different sizes of forearms may be measured by using a single photoelectric sensor retainer 16.

The band 90 of FIG. 5 may be divided into two bands between both edges 91 and 92. The ring formed of the pedestal 20 and the band 90 may be opened and closed by separating and combining the two bands. The band 90 may be a combination of a buckle and a clamping-bar or a fastener. Thus, the photoelectric sensor retainer 16 may be readily attached to and detached from the forearm.

In FIG. 5, pins 36 and 37 are mounted in the holes 28b and 29b of the adjusting units 28 and 29. Holes (not shown) through which the pins 36 and 37 respectively pass may be formed in the edges 91 and 92 of the band 90. As shown in FIG. 4, the pins 36 and 37 may be mounted in the holes 28c and 29c that are far from the principal plane 18, which will be described in detail with reference to FIGS. 6 and 7.

Figure 6:
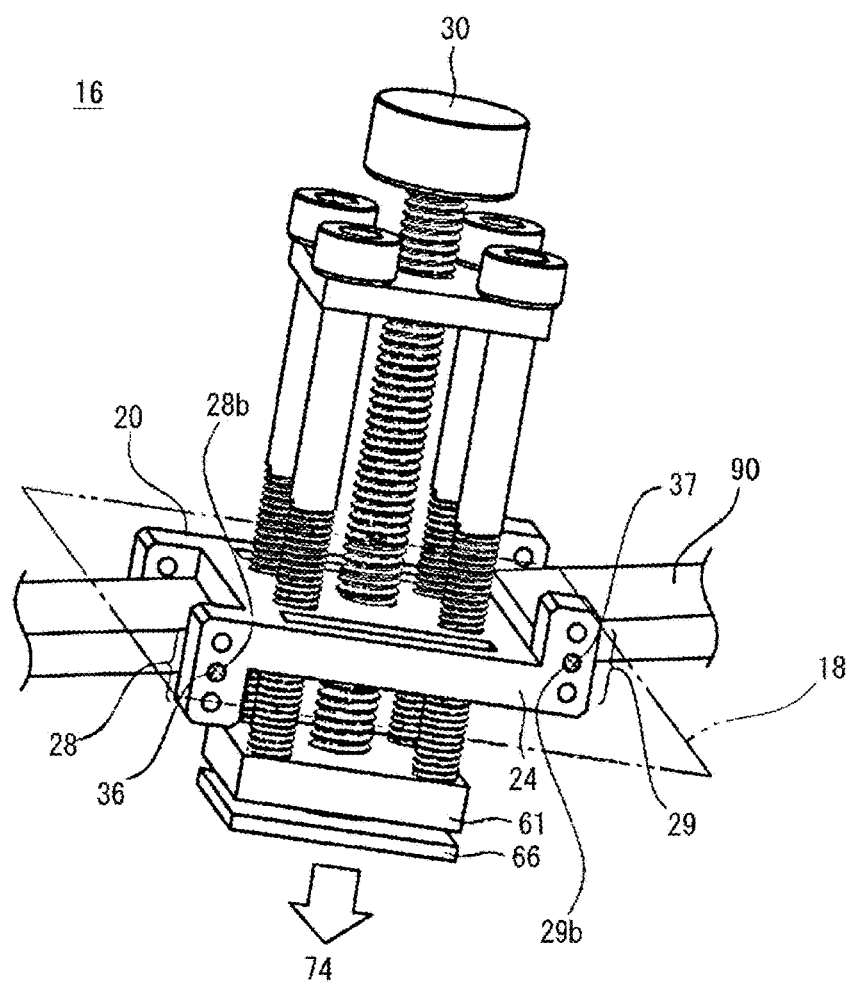
FIG. 6 is a perspective view of adjusting units of the photoelectric sensor retainer of FIG. 3.
Figure 7:
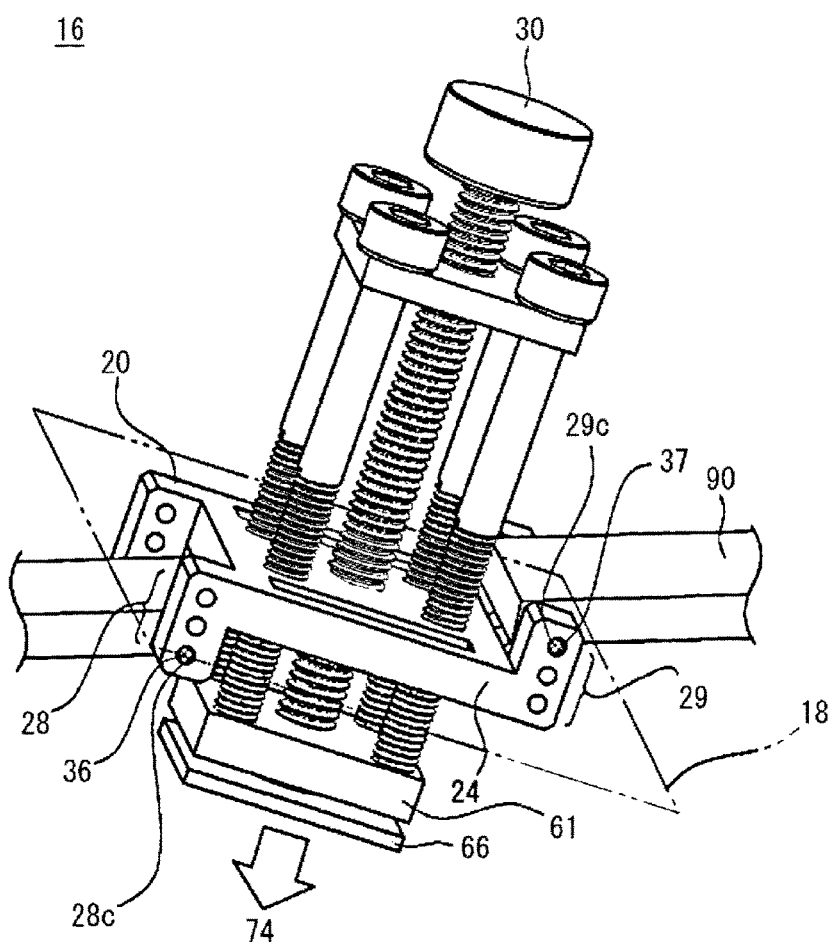
FIG. 7 is another perspective view of adjusting units of the photoelectric sensor retainer of FIG. 3.

FIG. 6 is a perspective view of the adjusting units 28 and 29 of the photoelectric sensor retainer 16 of FIG. 3, and FIG. 7 is another perspective view of the adjusting units 28 and 29 of the photoelectric sensor retainer 16 of FIG. 3. The adjusting units 28 and 29 respectively control an inclination between the principal plane 18 of the seating plate 24 and a plane that includes rotational axes related to the pins 36 and 37. The adjusting units 28 and 29 adjust a distance between the rotational axes related to the pins 36 and 37 and the principal plane 18 of the seating plate 24 of FIG. 4. The pins 36 and 37 temporarily fix the inclination described above. That is, the pins 36 and 37 fix the inclination while measuring a pulse wave.

In FIG. 6, the pins 36 and 37 are mounted in the holes 28b and 29b. As shown in FIG. 4, the holes 28b and 29b are closer to the principal plane 18 than the holes 28c and 29c, and farther from the principal plane 18 than the holes 28a and 29a.

As the selection of the mounting location of the pins 36 and 37 of FIG. 6, an inclination may be formed between the principal plane 18 and a plane that includes rotational axes related to the pins 36 and 37. The inclination may be, for example, greater than 0° and smaller than 20°. Also, a step difference may be formed between the principal plane 18 and the plane that includes rotational axes related to the pins 36 and 37.

In FIG. 7, the pins 36 and 37 are mounted in the holes 28c and 29c. As shown in FIG. 4, the holes 28c and 29c are farther from the principal plane 18 than the holes 28a and 29a and the holes 28b and 29b. Accordingly, as shown in FIG. 7, as the selection of the mounting location of the pins 36 and 37, an inclination greater than the inclination shown in FIG. 6 may be provided between the principal plane 18 and the plane that includes rotational axes related to the pins 36 and 37.

In FIG. 6, the pins 36 and 37 may be mounted on an asymmetrical location with respect to the center of the pedestal 20. For example, when the pin 36 is mounted in the hole 28b, the pin 37 may be mounted in the hole 29a or 29c. When the pin 37 is mounted in the hole 29b, the pin 36 may be mounted in the hole 28a or 28c.

Also, in FIG. 7, when the pin 36 is mounted in the hole 28c, the pin 37 may be mounted in the hole 29a. When the pin 37 is mounted in the hole 29c, the pin 36 may be mounted in the hole 28a. As shown in FIG. 3, no inclination may be provided.

Referring back to FIG. 5, in the photoelectric sensor retainer 16, the adjusting units 28 and 29 that include the holes 28b and 29b are suitable for pressing the light-receiving surface 77 in a perpendicular direction with respect to the skin surface 96. That is, the adjusting units 28 and 29 may rotate the light-receiving surface 77 around an axis parallel to the radial artery 97.

The radial artery 97 shown in FIG. 5 is a separated location from a long axis or a short axis of an oval shape cross-section of the forearm. The adjusting units 28 and 29 are suitable for pressing the photoelectric sensor 75 in a perpendicular direction with respect to the skin surface 96 near the radial artery 97. The adjusting units 28 and 29 may also be suitable when a plane that includes the rotational axes related to the pins 36 and 37 and the skin surface 96 is not parallel.

To maintain appropriate directions of the light-receiving surface 77 on every forearm 95 of persons under examination, as described above, the adjusting units 28 and 29 may have holes that may be selected besides the holes 28*b* and 29*b*.

As depicted in FIG. 5, the photoelectric sensor retainer 16 enables measuring a pulse wave by pressing the photoelectric sensor 75 on an artery of a wrist including the radial artery 97. At this point, because the photoelectric sensor retainer 16 includes the suspension device 40 and the adjusting units 28 and 29, appropriate directions of the light-receiving surface 77 may be maintained. The definition of the maintaining appropriate directions of the light-receiving surface 77 is described above.

As in FIG. 5, the skin surface 96 and the light-receiving surface 77 tightly contact each other in a state that the light-receiving surface 77 maintains an appropriate direction. Accordingly, the ratio of signal and noise may be reduced, or the occurrence of new noise by the external disturbance light may be prevented.

According to the current exemplary embodiment, a structure of a photoelectric pulse wave measuring apparatus that may precisely measure a pulse wave when the photoelectric sensor 75 is mounted on the photoelectric sensor retainer 16 is provided by reducing the weight of the photoelectric sensor retainer 16 to be suitable for carry.

Another exemplary embodiment will be described with reference to FIGS. 8 through 10.

Figure 8:
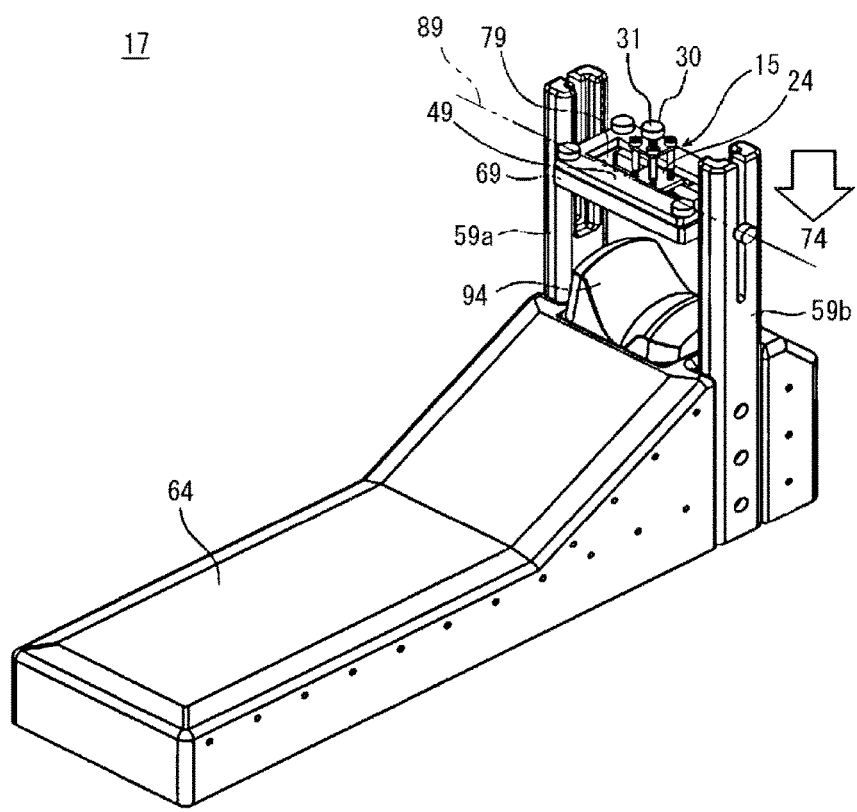
FIG. 8 is a perspective view of a photoelectric sensor retainer according to another exemplary embodiment.

FIG. 8 is a perspective view of a photoelectric sensor retainer 17 according to another exemplary embodiment. The photoelectric sensor retainer 17 includes the retainer 15 of FIG. 2. The photoelectric sensor retainer unit 17 is different from the photoelectric sensor retainer unit 16 of FIG. 3 in that the photoelectric sensor retainer 17 includes a stage 69, supporting columns 59*a* and 59*b*, and a forearm supporter 64 instead of the adjusting units 28 and 29.

In describing the photoelectric sensor retainer 17 of FIG. 8, the descriptions of the constituent elements that are identical to those of the photoelectric sensor retainer 16 (refer to FIGS. 3 through 7) according to the previous exemplary embodiment will not be repeated. The photoelectric sensor retainer 17 may be used as a photoelectric pulse wave measuring apparatus by mounting a photoelectric sensor and light emitters, as similar to the previous exemplary embodiments. The photoelectric sensor retainer 17 may be suitable for using in a stationary photoelectric pulse wave measuring apparatus.

Figure 9:
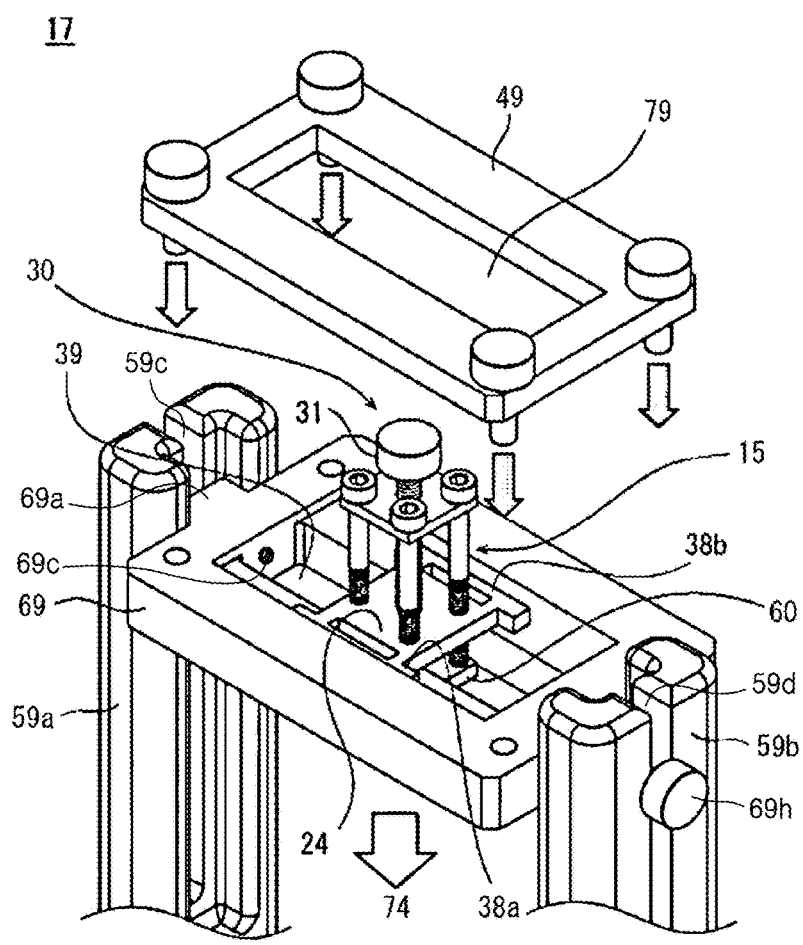
FIG. 9 is a partial magnified perspective view of the photoelectric sensor retainer of FIG. 8.

FIG. 9 is a partial magnified view of the photoelectric sensor retainer 17 of FIG. 8. The stage 69 supports a pedestal that includes the seating plate 24. The pedestal that includes the seating plate 24 includes edge units 38*a* and 38*b*. The edge unit 38*a* and 38*b* may have a width greater than that of a center portion of the seating plate 24. When the retainer 15 is mounted on the stage 69, the stage 69 supports the edge units 38*a* and 38*b*. Accordingly, the retainer 15 may be safely mounted on the stage 69.

As shown in FIG. 8, the photoelectric sensor retainer 17 includes a cover 49. As shown in FIG. 9, the cover 49 is mounted on upper surface of the stage 69. The cover 49 includes an opening 79. The opening 79 passes through the cover 49. A length direction of the opening 79 may be parallel to a length direction of an opening 39 formed in the stage 69.

As shown in FIG. 9, the opening 39 passes through the stage 69. A length direction of the opening 39 may be substantially perpendicular to a length direction of the forearm supporter 64 as shown in FIG. 8, that is, to an extension direction of a radial artery of a forearm.

As depicted in FIG. 9, the mounting unit 60 is located in the opening 39 or below a lower surface of the stage 69 outside the opening 39. Accordingly, the mounting unit 60 faces a skin surface of a forearm that is fixed on the forearm supporter 64.

As depicted in FIG. 8, the pressing unit 30 is located in the opening 79 or above an upper surface of the cover 49 outside the opening 79. Accordingly, the head unit 31 of the pressing unit 30 is exposed on an upper surface of the cover 49. Therefore, after mounting the cover 49 on the stage 69, the pressing unit 30 may be operated to press the mounting unit 60.

The retainer 15 depicted in FIGS. 8 and 9 is able to slide in a length direction of the opening 39 and the opening 79. Accordingly, when the photoelectric sensor retainer 17 is viewed from above, a location relationship between a region where a pulse wave is measured and the location of a photoelectric sensor mounted on the retainer 15 may be arbitrary adjusted.

As depicted in FIG. 9, the mounted cover 49 presses the edge unit 38*a* and 38*b* against the stage 69. At this point, the cover 49 limits a sliding of the retainer 15 on the opening 39. Accordingly, the adjusted location relationship may be stably maintained. Instead of the cover 49, the pedestal that includes the seating plate 24 may be temporarily fixed on the stage 69 by using screws or pins.

Referring to FIG. 8, the forearm supporter 64 is located in the measuring direction 74 with respect to the mounting unit 60 (referring to FIG. 2) that is included in the retainer 15. The forearm supporter 64 supports a forearm so that the radial artery of the forearm faces the mounting unit 60. Accordingly, when the photoelectric sensor retainer 17 is viewed from above, a location relationship between a region where a pulse wave is measured and a location of a photoelectric sensor mounted on the retainer 15 may be stably maintained.

The supporting columns 59*a* and 59*b* of FIG. 8 support the stage 69. The stage 69 may be movable in the measuring direction 74 or in an opposite direction to the measuring direction 74 with respect to the supporting columns 59*a* and 59*b*. That is, the stage 69 may be moved upward and downward directions. Accordingly, when the photoelectric sensor retainer 17 is viewed from a side, a location relationship between a region where a pulse wave is measured and the location of a photoelectric sensor mounted on the retainer 15 may be arbitrary adjusted.

The stage 69 of FIG. 8 may be rotatable around a rotational axis 89. The rotational axis 89 is perpendicular to a plane that is parallel to a length direction of the forearm supporter 64 and the direction of the measuring direction 74.

Figure 10:
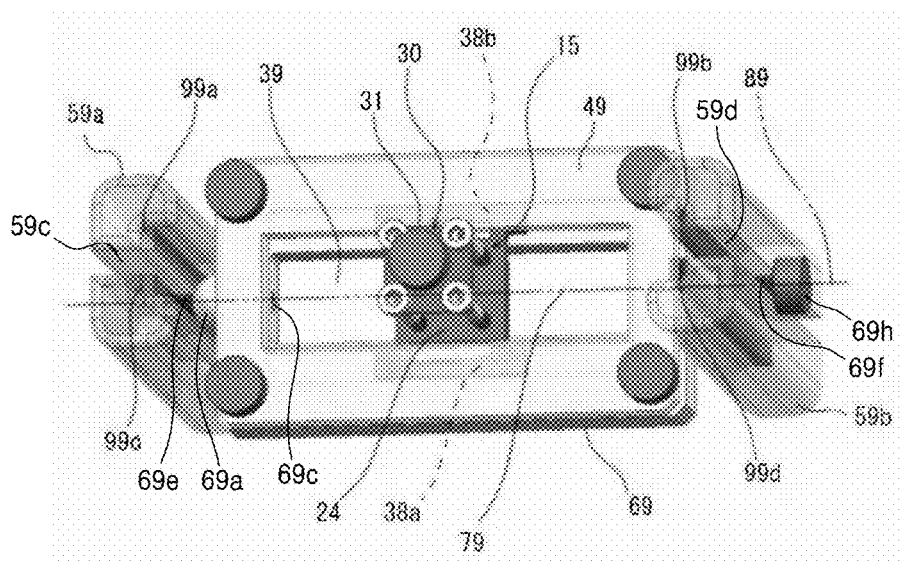
FIG. 10 is a partial magnified plan view of the photoelectric sensor retainer of FIG. 9.

FIG. 10 is a partial magnified plan view of the photoelectric sensor retainer 17 of FIG. 9. The rotational axis 89 is parallel to a direction in which the supporting columns 59*a* and 59*b* face each other.

Protrusion portions 69*a* respectively may be formed on both sides of the stage 69 facing each other. The protrusion portions 69*a* are supported in vertical grooves 59*c* and 59*d* of the supporting columns 59*a* and 59*b*. The protrusion portions 69*a* are formed along the rotational axis 89, and have a cylindrical shape or a hemisphere shape. Accordingly, the stage 69 may rotate around the rotational axis 89. Holes 69c having thread grooves may be formed in the protrusion portions 69a and in both sides of the stage 60 that contacts the protrusion portions 69a. Bolts 69e and 69f may fix the stage 69 on the supporting columns 59a and 59b by combining with the thread grooves formed on the hole 69c. After adjusting a vertical position of the stage 69 by rotating a head unit 69h that is formed on the bolts 69e and 69f, the position of the stage 69 may be fixed on the supporting columns 59a and 59b by rotating the head unit 69h of the bolts 69e and 69f.

The photoelectric sensor retainer 17 of FIG. 10 includes spacers 99a, 99b, 99c, and 99d between the supporting columns 59a and 59b and the stage 69. In FIG. 10, the supporting column 59a includes the spacers 99a and 99c, and the supporting column 59b includes the spacers 99b and 99d. The spacers 99a and 99c and the spacers 99b and 99d respectively contact and support the protrusion portion 69a of the stage 69.

An unintentional rotation of the stage 69 and the retainer 15 may be prevented by the bolts 69e and 69f. The force for preventing the unintentional rotation of the stage 69 and the retainer 15 may be increased by forming the spacers 99a, 99b, 99c, and 99d using a material having a large friction, for example, rubber.

Referring to FIG. 8, the supporting columns 59a and 59b are directly or indirectly connected to the forearm supporter 64. The location relationship between the supporting columns 59a and 59b and the forearm supporter 64 may be temporarily or permanently fixed. The location relationship between the stage 69 and the supporting columns 59a and 59b may be temporarily fixed. Accordingly, although the pressing unit 30 presses the mounting unit 60 and to the skin surface of the forearm, the adjusted location relationship may be stably maintained as described above. Also, the supporting columns 59a and 59b may be linear columns or bended columns.

The forearm supporter 64 of FIG. 8 further includes a wrist supporter 94. The wrist supporter 94 faces the mounting unit 60 that is included in the retainer 15. Accordingly, the forearm supporter 64 may allow the skin surface located immediately on the radial artery to face the light-receiving surface of the photoelectric sensor that is mounted on the mounting unit 60.

The photoelectric sensor retainer 17 of FIG. 8 is suitable for measuring a pulse wave by pressing the photoelectric sensor on a wrist artery including the radial artery. At this point, because the photoelectric sensor retainer 17 includes the suspension device 40 and the forearm supporter 64, an appropriate direction of the light-receiving surface 77 may be maintained. The definition of the maintaining of the appropriate direction of the light-receiving surface 77 is described above.

However, the current exemplary embodiment is not limited thereto, and thus, the exemplary embodiment may be appropriately modified within the scope of the exemplary embodiment. The photoelectric sensor retainer related to the current exemplary embodiment may be referred to as a jig that is used when a performance of the photoelectric sensor is tested or when data collected by the photoelectric sensor are compared.

The retainer 15 of FIG. 2 may also be used as a sensor jig for maintaining an appropriate direction of a light-receiving surface. The photoelectric sensor retainers 16 and 17 shown in FIGS. 3 through 10 may also be used as measuring jigs for maintaining an appropriate direction of a light-receiving surface. The photoelectric sensor retainers 16 and 17 may increase measuring reproducibility in testing performance or comparison of data.

For example, data collected by the photoelectric sensor retainer 16 of FIG. 3 and data collected by the photoelectric sensor retainer 17 of FIG. 8 may be compared. Therefore, a performance difference of the photoelectric sensor when the photoelectric sensor is mounted on a portable photoelectric pulse wave measuring apparatus and when the photoelectric sensor is mounted on a stationary type photoelectric pulse wave measuring apparatus may be measured.

Also, to convert a pulse wave to a blood pressure, a data base is used. When the photoelectric sensor retainer according to the exemplary embodiment is used as a jig, a precision of data collection for constructing the data base may be increased. This is because the photoelectric sensor retainer according to the exemplary embodiment steadily maintains a pressure that is applied to the blood vessel during measuring a pulse wave and a direction of the blood vessel.

The pressing unit 30 of FIG. 2 may be a cylinder that is operated by a fluid that includes air and a length of which varies.

The holes 28a, 28b, and 28c and the holes 29a, 29b, and 29c, respectively may be a single long hole. That is, the inclination of the principal plane 18 may be adjusted without steps. In this case, a fixing unit may be provided on the pins 36 and 37 of FIG. 3 and the single long hole. Also, an element for measuring the inclination may be provided.

When a photoelectric sensor is mounted on the photoelectric sensor retainer according to the exemplary embodiment, a waveform of a pulse wave may be precisely measured.

While one or more exemplary embodiments have been described with reference to the figures, it will be understood by those of ordinary skill in the art that various changes in form and details may be made therein without departing from the spirit and scope as defined by the following claims.

What is claimed is:

1. A photoelectric sensor retainer comprising:
   a sensor mounting unit on which a photoelectric sensor having a light-receiving surface is attachable and detachable, the light-receiving surface facing a measuring direction;
   a pressing unit configured to press an upper surface of the sensor mounting unit in the measuring direction to apply pressure to the sensor mounting unit;
   a pedestal comprising a seating plate configured to support the pressing unit, the seating plate having a principal plane perpendicular to a pressing direction of the pressing unit; and
   a suspension device configured to support the sensor mounting unit,
   wherein the suspension device comprises:
      a frame disposed to face the sensor mounting unit with the seating plate therebetween; and
      links configured to connect the frame and the sensor mounting unit, and pass through the seating plate.

2. The photoelectric sensor retainer of claim 1, wherein the pressing unit is a screw combined with the seating plate, and
   an edge of the pressing unit is configured to press the upper surface of the sensor mounting unit while the pressing unit is rotated to adjust a distance between the seating plate and the upper surface of the sensor mounting unit.

3. The photoelectric sensor retainer of claim 1, further comprising coil springs surrounding the links between the seating plate and the frame, the coil springs being configured to repulse the sensor mounting unit in a direction opposite to the measuring direction.

4. The photoelectric sensor retainer of claim 1, wherein the links comprise four or more links, and
the links surround the pressing unit.

5. A photoelectric sensor retainer comprising:
a sensor mounting unit on which a photoelectric sensor having a light-receiving surface is attachable and detachable, the light-receiving surface facing a measuring direction;
a pressing unit configured to press an upper surface of the sensor mounting unit in the measuring direction to apply pressure to the sensor mounting unit;
a pedestal; and
a band connected to the pedestal,
wherein the pedestal comprises:
a seating plate configured to support the pressing unit, the seating plate having a principal plane perpendicular to a pressing direction of the pressing unit;
adjusting units, each of the adjusting units being configured to adjust an angle between the principal plane and a plane of the band; and
wings disposed on respective edges of the seating plate, ends of the band are connected to the respective wings, the measuring direction are oriented inside a ring that is formed by the band and the pedestal, and
the pedestal is configured to rotate around each of the wings with respect to the band.

6. The photoelectric sensor retainer of claim 5, wherein the adjusting units are disposed on the respective wings, and
each of the adjusting units is configured to adjust a distance between a rotational axis of a respective one of the wings and the principal plane.

7. The photoelectric sensor retainer of claim 6, further comprising pins, each of the pins forming the rotational axis,
wherein each of the adjusting units comprises holes having respective distances from the principal plane, and
each of the pins is configured to be attached to and detached from a respective one of the holes.

8. The photoelectric sensor retainer of claim 1, wherein the sensor mounting unit comprises:
a base unit;
a sensor supporting unit disposed on a side of the base unit in the measuring direction, the sensor supporting unit comprising a sensor supporting surface disposed to face the measuring direction; and
a piezoelectric element disposed between the base unit and the sensor supporting unit.

9. A photoelectric sensor retainer comprising:
a sensor mounting unit on which a photoelectric sensor having a light-receiving surface is attachable and detachable, the light-receiving surface facing a measuring direction;
a pressing unit configured to press an upper surface of the sensor mounting unit in the measuring direction to apply pressure to the sensor mounting unit;
a pedestal comprising a seating plate configured to support the pressing unit, the seating plate having a principal plane perpendicular to a pressing direction of the pressing unit;
a stage configured to support the pedestal;
a forearm supporter disposed on a side of the sensor mounting unit in the measuring direction, the forearm supporter being configured to support a forearm so that a radial artery of the forearm faces the sensor mounting unit; and
supporting columns configured to support the stage, the supporting columns being connected to the forearm supporter,
wherein the stage is configured to move in the measuring direction and in a direction opposite to the measuring direction with respect to the supporting columns.

10. The photoelectric sensor retainer of claim 9, wherein the stage is configured to rotate around a rotational axis perpendicular to a plane parallel with a length direction of the forearm supporter and the measuring direction.

11. The photoelectric sensor retainer of claim 10, wherein the stage comprises protrusion portions extending in a direction of the rotational axis toward the supporting columns,
the supporting columns comprise respective grooves corresponding to the respective protrusion portions, and
the protrusion portions are connected to the respective supporting columns by respective fixing elements configured to fix locations of the respective protrusion portions on the respective supporting columns and rotating locations of the respective protrusion portions with respect to the rotational axis.

12. A photoelectric pulse wave measuring apparatus comprising:
the photoelectric sensor retainer of claim 8; and
a photoelectric sensor having the light-receiving surface and a substrate surface on a side opposite to the light-receiving surface, the photoelectric sensor disposed on the sensor supporting surface,
wherein the substrate surface is disposed to face the sensor supporting surface.

* * * * *